(12) United States Patent
Hoogland

(10) Patent No.: US 10,537,241 B1
(45) Date of Patent: Jan. 21, 2020

(54) SUBJECTIVE OPTOMETER FOR HOME USE

(71) Applicant: Jan Hoogland, Carmel, CA (US)

(72) Inventor: Jan Hoogland, Carmel, CA (US)

( * ) Notice: Subject to any disclaimer, the term of this patent is extended or adjusted under 35 U.S.C. 154(b) by 0 days.

(21) Appl. No.: 16/164,797

(22) Filed: Oct. 19, 2018

(51) Int. Cl.
| | |
|---|---|
| *A61B 3/028* | (2006.01) |
| *A61B 3/06* | (2006.01) |
| *A61B 3/00* | (2006.01) |
| *A61B 3/09* | (2006.01) |
| *A61B 3/08* | (2006.01) |

(52) U.S. Cl.
CPC ............ *A61B 3/028* (2013.01); *A61B 3/0008* (2013.01); *A61B 3/0016* (2013.01); *A61B 3/06* (2013.01); *A61B 3/09* (2013.01); *A61B 3/08* (2013.01)

(58) Field of Classification Search
CPC ....... A61B 3/032; A61B 3/028; A61B 3/0025; A61B 3/024; A61B 3/0285
USPC ...................................................... 351/222
See application file for complete search history.

(56) References Cited

U.S. PATENT DOCUMENTS

| | | | | |
|---|---|---|---|---|
| 3,843,240 A | * | 10/1974 | Cornsweet | A61B 3/09 351/203 |
| 2003/0197856 A1 | * | 10/2003 | Milanich | A61B 3/028 356/128 |
| 2012/0249769 A1 | * | 10/2012 | Naba | A61B 3/102 348/78 |

* cited by examiner

*Primary Examiner* — Mohammed A Hasan
(74) *Attorney, Agent, or Firm* — Suiter Swantz pc llo

(57) ABSTRACT

The unsuitability of the retina of the eye as a reflective projection screen for image observation causes objective optometry to be expensive and of limited accuracy. The subjective assessment of image quality is the only way to make full use of the resolution capability of the eye. A subjective optometer for home use is disclosed with ample accuracy and confidence for mail order of prescription glasses. It overcomes the disadvantages of subjective optometry and is able to measure the refractive errors to the resolution limit of the eye, which is of great importance for the present state and relief of ametropia. Electronic recording and connectivity can be provided as an option.

9 Claims, 2 Drawing Sheets

SUBJECTIVE OPTOMETER FOR HOME USE

CROSS-REFERENCE TO RELATED APPLICATIONS

KNIGHT, SAM, "The spectacular power of Big Lens", The Guardian, May 10, 2018 article: https://www.theguardian.com/news/2018/may/10/the-invisible-power-of-big-glasses-eyewear-industry-essilor-luxottica Smart Vision Labs Releases Next Generation Wavefront Autorefractor Jul. 27, 2017 announcement: https://www.smartvisionlabs.com/news/next-generation-wavefront-autorefractor-available/

DAVE, TRUSIT, "Automated Refraction. Design and Application", Jun. 4, 2004 article: http://www.adh-trade.com/PDF/Augen/Autom_Refraction.pdf SMITH, GEORGE (University of Melbourne) & ATCHISON, DAVID A. (Queensland University of Technology), 1997, Cambridge University Press, *The Eye and Visual Optical Instruments*: https:/www.cambridge.org/core/books/the-eye-and-visual-optical-instruments/910C5FCC5EBA1A81B08C68C3DA3CFFB 1951 USAF Resolution Test Chart, Wikipedia: https://en.wikipedia.org/wiki/1951_USAF_resolution_test_chart

BACKGROUND OF THE INVENTION

Vision is a very precious possession. The quality of our vision is such that what we see we consider to be reality, in contrast to any other image that mankind is able to produce. It is very difficult to imagine that what we see is actually just an image projected in our brain.

Optometry is an important guardian of the quality of that image in our brain. The present state of optometry is dramatically presented in The Guardian's May 10, 2018 article, "The spectacular power of Big Lens". It calls out "the accelerating degradation of our eyes" and states, "Vision campaigners forecast that the myopia epidemic will put enormous strain on health systems across the developing world, which are already unable to equip their populations with a medical device that has been around since the Middle Ages." This crisis calls for a reassessment of what optometry can do for us.

The thermometer is a home use device that measures temperature, providing us with the ability to make important decisions for our well-being. Blood pressure monitors and many other devices provide the same benefit. Unfortunately, an optometer for home use to measure ametropia, that is the presence of refractive errors of the eye, is not available, although it clearly is very much needed.

Optometry is concerned with the measurement of the refractive errors of the eye, such as being out of focus and astigmatism. Optometry is practiced by optometrists and ophthalmologists; the latter profession includes the ability to perform eye surgery. To obtain an assessment of the state of personal ametropia, a visit to an optometrist is presently the only option. It is a significant inconvenience and expense, as compared to other measurements of important bodily data. Considering the present occurrence of ametropia, it is very desirable to be able to make an assessment ourselves, as is done with so many other health conditions.

Optometry is executed objectively and subjectively. The objective method is performed by an optometer called an autorefractor in which the image assessment is based on electronic processing. A test arrangement produces a suitable image on the retina for the measurement of the refractive errors of the eye. The reflection of this image on the retina is made accessible via a beam splitter for processing. The optometer does this work without assistance from the optometrist or the patient and is commonly called an autorefractor. An arrangement is shown in FIG. 1.

The main problem with the objective approach is that the quality of the retina as a reflective projection screen is exceedingly poor. This is to be expected because it is a transmission screen, not a reflective projection screen. The unsuitability of the retina as a reflective projection screen is thus a major and unavoidable limitation of the objective measurement of refractive errors. As the objective measurement may therefore lack accuracy or reliability, it is followed up by a subjective method of measuring the refractive errors.

BRIEF SUMMARY OF THE INVENTION

The subjective method relies on the judgment of the patient to assess the image quality and is therefore called subjective. The traditional subjective test consists of an examination by the optometrist by means of a phoropter and is regarded as a fine-tuning of the measurement provided by the autorefractor. The examination relies on the opinion of the patient on the image quality of the characters presented. The traditional subjective measurement has the following deficiencies:

- The inexperience or haphazardness of the patient to evaluate a complex image.
- The use of characters for the test, which engages the accommodation of the eye.
- The occurrence of instrument myopia and situation myopia.
- The large amount of time and patience required to arrive at a final evaluation.
- The evaluation needs to take place at a relatively high level of illumination, which reduces the operating aperture of the eye.
- Optometric service is out of reach for the majority of people in this world, both financially and physically.

The objective and subjective methods together enable the optometrist to provide a prescription for corrective glasses of sufficient accuracy and reliability. However, considering the present state of ametropia, a subjective optometer for home use that provides accurate and reliable assessment of the refractive errors of the eye is very much needed.

The present invention employs the superior accuracy of the subjective method over the accuracy of the objective method and overcomes all the deficiencies of the traditional examination by means of a phoropter. This is achieved by providing:

- a test object which allows the assessment of the image quality to be of objective quality.
- a test object which allows measurements to the full resolution capability of the eye.
- a test object which prevents the eye from focusing.
- a combination of test objects which provides the correlation between the optimum test result for reading purposes and the optimum test result for other test purposes.
- a numerically controllable test environment of light intensity, color and numerical aperture.

The Subjective Optometer for Home Use consists of a rotational test object containing a point light source, an orientation marker and an USAF-1951 Airforce Resolution Chart type of target, a focusing means and a collimator. All measurements are made by the user. A typical arrangement is shown in FIG. 4.

DETAILED DESCRIPTION OF THE INVENTION

Figure 1:
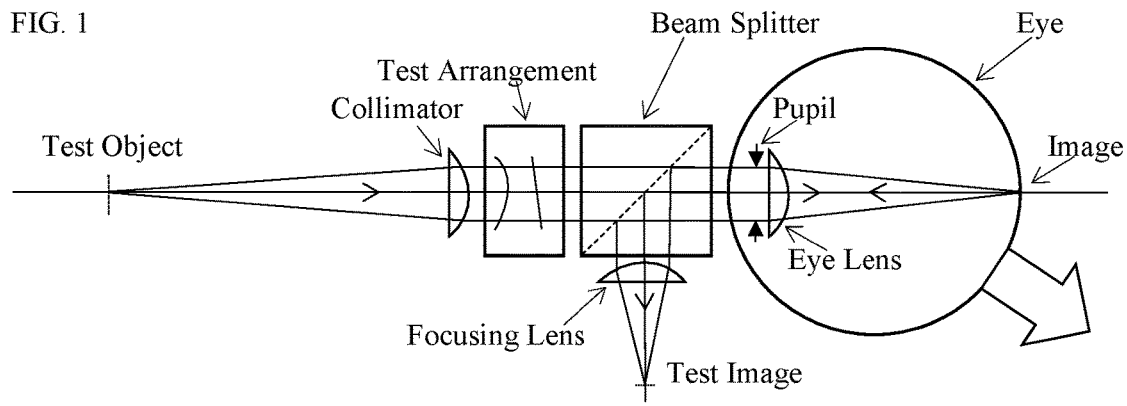
FIG. 1 is a general sketch of an autorefractor. The image of a test object is projected via a test arrangement on the retina of the eye. The reflection of the image of the test object from the retina is made accessible via a beam splitter for electronic processing. The very poor quality of the reflected test image on the retina limits the accuracy of the objective test method and incurs considerable complexity and expense to obtain acceptable accuracy of the measurements.
Figure 2:
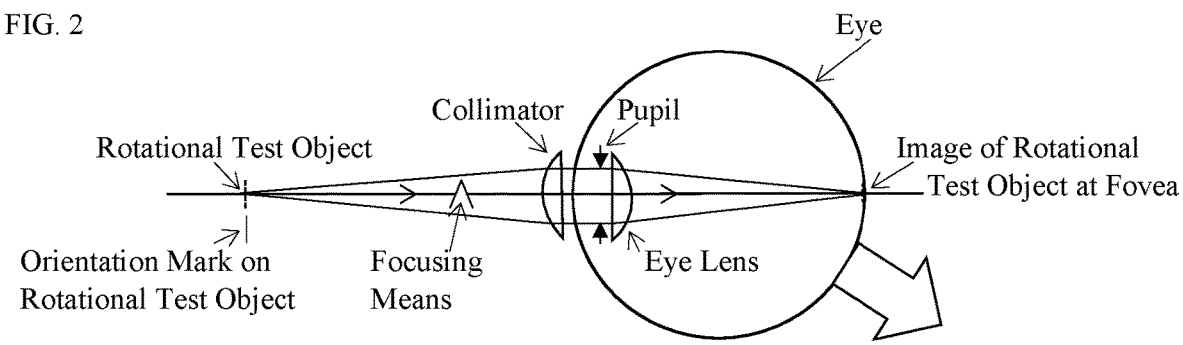
FIG. 2 exemplifies the Subjective Optometer for Home Use test method, which is based on the judgment of the user to assess the image quality of the test object on the retina. This arrangement evaluates an image to the resolution limit of the eye. The focusing means measures the refractive errors which are focal error and astigmatism. The rotational object with an orientation mark determines the orientation of astigmatism.
Figure 3:
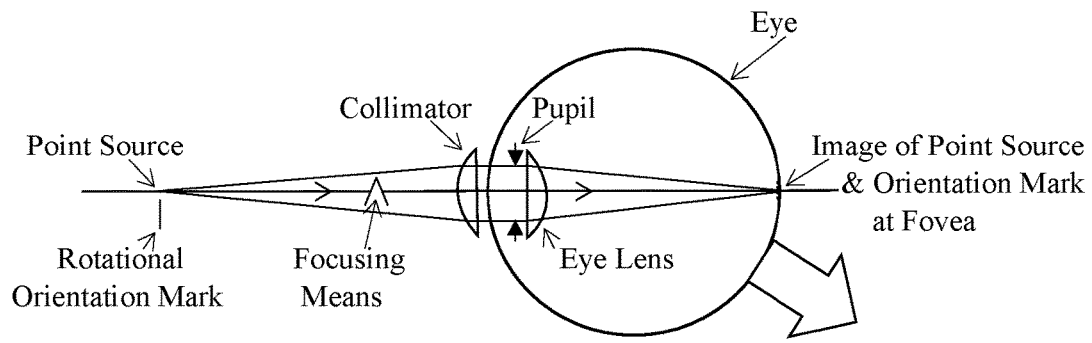
FIG. 3 shows the choice of a simple test object like a point light source which greatly reduces the subjectivity of the evaluation of the image quality because the only requirement of the user is to determine the smallest line width of the image. The orientation marker in the test object determines the orientation of astigmatism. The image of a point light source lacks detail that would trigger the eye to focus. The refractive errors can be measured in a stress-free home environment.

The unsuitability of the retina as a reflective screen to observe an image limits the accuracy of objective measurement to measure refractive errors of the eye. It causes the autorefractor to be technically complicated and consequently expensive. The subjective measurement is the only way to assess the image quality to the limit of the resolution capability of the eye. The problems of the subjective method, as listed in the Background of the Invention section, are overcome by an arrangement in which a point light source is projected on the retina, as shown in FIG. 3.

The subjectivity of the measurement is overcome by using a very simple object, like a point source, as a test object. A point source as a test object is a light emitting area of sufficiently small size and shape as to not significantly degrade the intended measurement at hand. The image of a point source on the retina of an eye that contains refractive errors can generally be focused to two line images at different focal positions. The focal positions determine the refractive errors and their difference is a measure of astigmatism. Alignment of the orientation marker with the orientation of the astigmatism of the point source image by a rotation of the target measures the orientation of the astigmatism. The only other requirement from the user then is to determine the smallest line width of the image, which is very close to being objective. The absence of detail of the in-focus and out-of-focus point source images prevents accommodation of the eye. The testing at night or in a darkened room, when the eye is in its rest position, provides the optimum circumstances for high accuracy measurements and high repeatability. An accuracy of 0.12 diopter is achievable, while 0.08 diopter can be reached after some practice. These numbers are well within the accuracy required for a custom prescription and are usable for many test purposes.

Figure 4:
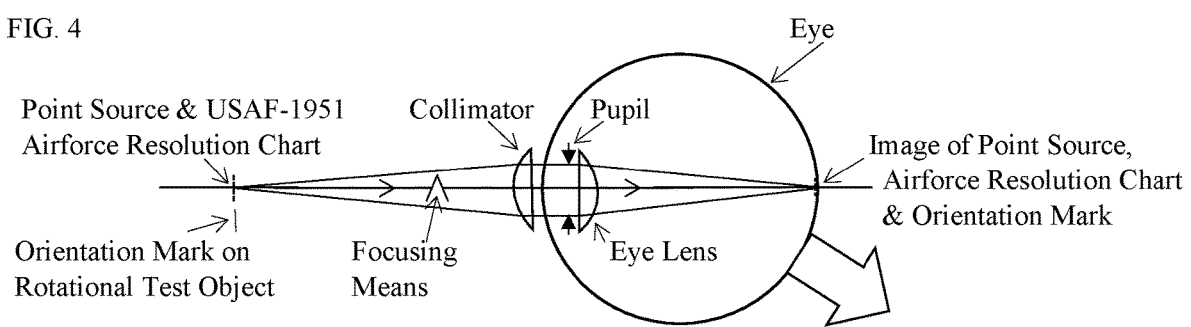
FIG. 4 shows a more complete setup in which the point light source and the USAF-1951 Airforce Resolution Chart type of target are set side-by-side in the test object. It correlates the test results of the point light source measurement with the Airforce Resolution Chart test, which increases the confidence in the test results. Separate light control provides the optimum illumination, either for optimal reading ability or for optimal accuracy to observe small changes. The dual tests ability is ideal for home use. The optometer is a simple instrument that is readily understood, easy to operate and adaptable to varying light conditions.

FIG. 4 shows the present invention which employs a USAF-1951 Airforce Resolution Chart type of target to determine the optimal focus for reading material. After angular alignment of the Chart with the astigmatism caused by the eye, the optimum focus is determined for each astigmatic focus. The results can be compared with those obtained with the point source tests. The Chart is remarkably effective in removing the degradation of the astigmatism in each of the two orientations. The achieved resolution can be read from the Chart and remains valid after the astigmatism has been corrected by the prescription glasses. That results in that the test measures the resolution of the eye in case it did not have refractive errors. The test provides to express 20/20 vision in values of the USAF-1951 Airforce Resolution Chart. The accuracy of the USAF-1951 target is considerably better than a letter test like the Snellen Chart.

FIG. 4 also shows the combination of a point source and the USAF-1951 Airforce Resolution Chart type of target, providing an exact correlation between the optimal test results for a point light source and a test object for reading material. Separate numerical light control of the point source and the reading material test object will allow the point source test to be performed in total darkness to allow the pupil to open fully. The exact correlation provides confidence in the correct prescription for custom reading glasses, which is essential for mail order purposes. Fixed test circumstances are achieved with numerical control of the light levels, numerical aperture and color, which greatly increases the repeatability of the measurements.

Figure 5:
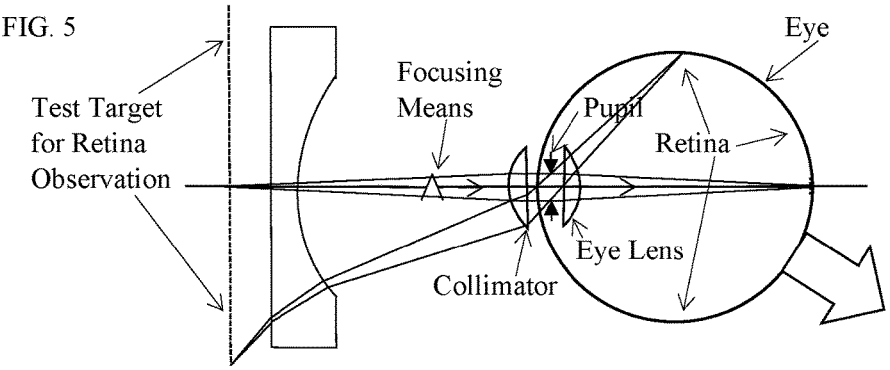
FIG. 5 shows a test object that covers the whole retina. It can be used to determine the field of view, the presence of glaucoma, the extent of color blindness, the extent of the fovea, the blind spot and show trouble areas of the retina.

FIG. 5 shows that the optometer can be equipped with a variety of additional test objects to provide measurement of the field of view, detect the blind spot, notice trouble areas of the retina and show the extent of glaucoma, the extent of color blindness and the extent of the fovea. A binocular version of the optometer provides a comparison of the two eyes, indicates alignment accuracy and shows the nature of a "lazy eye". The Subjective Optometer for Home Use provides an extensive and fascinating look on what is going on in our eyes. A drawing of what we see can alert the optometrist and ophthalmologist in their assessment of our eye problems.

The Subjective Optometer for Home use is sufficiently low in cost making it affordable for most households. Measurements can be made at the convenience and practicality of the home setting, where working conditions and needed darkness are readily available. It readily provides the measurements needed for a prescription for ordering glasses by mail. The optometer can also be used to check current prescription glasses as well as track developing changes in vision like myopia in children and presbyopia in adults.

The arrangement shown in FIG. 4 is of sufficient accuracy and reliability for ordering prescription glasses by mail, which greatly increases the availability and affordability. Additionally, the ability to provide an assessment that is precise to the limit of the vision of the patient is very useful. It will timely show the tendencies in the development of the refractive errors of the eye due to usage, child development and aging. Other benefits of this optometer are the ability to track the results of a test procedure, remedies and medical conditions. The present invention provides a Subjective Optometer for Home Use to address these needs. Means to electronically record the results may be added to the optometer as an option. Home use indicates that:

The device can be reliably operated by the average adult.

The measurement is reliable for making an important decision, like ordering prescription glasses by mail.

The device can be mass-produced at an affordable cost for the average household.

The advantages of this arrangement are summarized as follows:

Measurements can be made with the eye at the rest position, that is at total darkness, which is an essential requirement for reliable and repeatable values. Cycloplegia and dilation medicines are not needed.

Measurements can also be made under active circumstances if so desired, by activation of a different part of the test object and by making use of the various home conditions.

Measurements are made with an accuracy that makes full use of the resolution capability of the eye. An accuracy of 0.12 D is readily achievable and 0.08 D after some practice. The measurement criterion when using a point source, which is the minimum line width, is very nearly objective, as compared to the subjective "best picture" opinion of the patient with the optometrist. Also, the use of USAF-1951 Airforce Resolution Chart is considered to be close to being objective.

Defocus is shown as a circle and astigmatism as a line, together forming an illuminated undetailed area that does not trigger the eye to accommodate.

The full aperture of the pupil can be engaged because the overall light input is very small. The refractive errors are measured in otherwise total darkness. Measurements can also be made under actual lighting conditions, which reduces the pupil size. The test environment can be accurately controlled by a numerical control of the light intensity, the numerical aperture of the light source and the color of the test object illumination.

The accuracy is sufficiently high in order to timely observe small changes due to working conditions, like excessive close-up activity that may cause myopia, tests, experiments, medicines, circumstances and medical conditions.

Accurate chromatic aberrations can be measured by a change of color of the point source.

The present optometer is not limited by a finite step size.

The Subjective Optometer for Home Use can be executed as an inexpensive compact personal unit or as a high accuracy research tool.

The invention claimed is:

1. An optometer comprising:
a test object including a point light source; and
a collimator lens configured to direct light from the point light source to an eye of a user to allow the eye to generate an image of the point illumination source on a retina of the eye when the eye is in a rest position without triggering the eye to focus, wherein a position of the collimator lens is adjustable by the user, wherein a user-selected position of the collimator lens with respect to the point light source providing an in-focus image of the point light source as determined by the user is indicative of focal error in the eye.

2. The optometer of claim 1, wherein a difference between the user-selected position of the collimator lens and a nominal position of the collimator lens providing collimated light from the point light source to the eye is indicative of the focal error in the eye.

3. The optometer of claim 1, wherein the test object further comprises:
a linear orientation mark, wherein a rotation of the linear mark is adjustable by the user, wherein a user-selected rotation of the linear orientation mark providing a smallest line width of the linear orientation mark as determined by the user is indicative of an orientation of astigmatism in the eye.

4. The optometer of claim 1, wherein the test object further comprises:
a rotational orientation mark, wherein a user-identified direction of the rotational orientation mark providing a smallest line width of the rotational orientation mark as determined by the user is indicative of an orientation of astigmatism in the eye.

5. The optometer of claim 1, wherein a distance between two user-selected positions of the collimator lens with respect to the point light source corresponding to two in-focus line images of the point light source is indicative of a magnitude of astigmatism in the eye.

6. The optometer of claim 1, wherein the test object further comprises:
a resolution target, wherein the resolution target includes a plurality of test patterns, wherein at least some of the plurality of the test patterns include periodic linear marks with unique spatial frequencies, wherein a particular test pattern of the plurality of test patterns having a highest spatial frequency resolvable by the user is indicative of a resolution of the eye; and
an illumination source to illuminate the resolution target.

7. The optometer of claim 6, wherein at least one of an intensity, numerical aperture, or a spectrum of the illumination light source are adjustable.

8. The optometer of claim 1, wherein the test object further comprises:
a retina test target;
an illumination source to illuminate the retina test target; and
a retina observation lens positioned between the retina test target and the collimator lens, wherein the retina observation lens and the collimator lens image the retina test target onto a curved surface of the retina, wherein the image of the retina test target covers the retina.

9. An optometer comprising: a test object comprising: a point light source; and a linear orientation mark, wherein a rotation of the linear mark is adjustable by the user; and a collimator lens configured to direct light from the point light source to an eye of a user to allow the eye to generate an image of the point illumination source on a retina of the eye when the eye is in a rest position without triggering the eye to focus, wherein a position of the collimator lens is adjustable by the user, wherein a user-identified direction of the rotational orientation mark providing a smallest line width of the rotational orientation mark as determined by the user is indicative of an orientation of astigmatism in the eye, wherein a distance between two user-selected positions of the collimator lens with respect to the point light source corresponding to two in-focus line images of the point light source as determined by the user is indicative of a magnitude of astigmatism in the eye, wherein a difference between a nominal position of the collimator lens providing collimated light from the point light source to the eye and any of the two-user selected positions of the collimator lens is indicative of the focal error in the eye.

* * * * *